(12) United States Patent
Ma et al.

(10) Patent No.: US 8,236,779 B2
(45) Date of Patent: Aug. 7, 2012

(54) ANTIVIRAL NUCLEOSIDES

(75) Inventors: Han Ma, Passaic, NJ (US); Keshab Sarma, Kinnelon, NJ (US); David Bernard Smith, San Mateo, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 0 days.

(21) Appl. No.: 13/014,022

(22) Filed: Jan. 26, 2011

(65) Prior Publication Data
US 2011/0150829 A1    Jun. 23, 2011

Related U.S. Application Data

(60) Provisional application No. 61/299,229, filed on Jan. 28, 2010.

(51) Int. Cl.
*A01N 43/04* (2006.01)
*A61K 31/70* (2006.01)
*C07H 19/00* (2006.01)

(52) U.S. Cl. ........................................ 514/50; 536/28.53
(58) Field of Classification Search .................. None
See application file for complete search history.

(56) References Cited

U.S. PATENT DOCUMENTS 6,784,166 B2 * 8/2004 Devos et al. ............... 514/47
6,846,810 B2 * 1/2005 Martin et al. .............. 514/49

FOREIGN PATENT DOCUMENTS

| WO | WO 2004/046159 A1 | 6/2004 |
| WO | WO 2007/068615 A2 | 6/2007 |
| WO | WO 2009/069095 A2 | 6/2009 |

OTHER PUBLICATIONS (International Search Report for International Patent Application No. PCT/EP2011/050971), Mar. 2011.

\* cited by examiner

*Primary Examiner* — Traviss C McIntosh, III
(74) *Attorney, Agent, or Firm* — Brian L. Buckwalter

(57) ABSTRACT

Compounds having the formula I wherein $R^1$, $R^2$ and $R^3$ are as defined herein are Hepatitis C virus NS5*b* polymerase inhibitors. Also disclosed are compositions and methods for treating an HCV infection and inhibiting HCV replication.

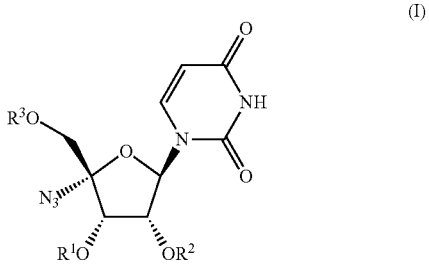

(I)

15 Claims, 6 Drawing Sheets

Phosphorylation of 4'-AU-(4'-Azido-uridine) in HCV replicon 2209-23 cells
(48 h incubation)

Phosphorylation of 4'-AU (4'-Azido-uridine) in primary human
hepatocytes (48 h incubation)

Phosphorylation of 4'-AU (4'-Azido-uridine) in human PBMCs (48 h incubation)

Phosphorylation of 4'-AC (4'-Azido-cytidine) in human PBMCs (1 h incubation)

Phosphorylation of 4'-AC (4'-Azido-cytidine) in human PBMCs (120 h incubation)

Phosphorylation of 4'-AU in primary human hepatocytes (48 h incubation)

Phosphorylation of 4'-AU (4'-Azido-uridine) in human bone marrow cells (BMCs) (48 h incubation)

Phosphorylation of 4'-AU (4'-Azido-uridine) in (PBMCs) (48 h incubation)

ANTIVIRAL NUCLEOSIDES

CROSS REFERENCE TO PRIOR APPLICATIONS

This application claims the benefit of priority to U.S. Ser. No. 61/299,229 filed Jan. 28, 2010 which is hereby incorporated by reference in its entirety.

FIELD OF THE INVENTION

The present invention provides acylated nucleosides which are prodrugs of an inhibitor of Hepatitis C Virus (HCV) RNA-dependent RNA viral polymerase. These compounds when administered orally are readily absorbed from the GI tract and efficiently revert to the parent nucleoside in the blood. These prodrugs are inhibitors of RNA-dependent RNA viral replication and are useful as inhibitors of HCV NS5B polymerase, as inhibitors of HCV replication, and for the treatment of hepatitis C infection in mammals. In particular, the invention is concerned with the use of acylated pyrimidine nucleoside compounds which provide improved drug absorption when the nucleoside is administered orally.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of-approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forns and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.,* 1999 19:5; Di Besceglie, A. M. and Bacon, B. R., *Scientific American, October:* 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.-Infect. Dis.* 2003 3(3):207-219.

Currently there are a limited number of approved therapies are currently available for the treatment of HCV infection. New and existing therapeutic approaches to treating HCV and inhibition of HCV NS5B polymerase have been reviewed: R. G. Gish, *Sem. Liver. Dis.,* 1999 19:5; Di Besceglie, A. M. and Bacon, B. R., *Scientific American,* October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patents on experimental therapy for hepatitis C virus infection (1999-2002), *Exp. Opin. Ther. Patents* 2003 13(11):1707-1723; F. F. Poordad et al. Developments in Hepatitis C therapy during 2000-2002, *Exp. Opin. Emerging Drugs* 2003 8(1):9-25; M. P. Walker et al., Promising Candidates for the treatment of chronic hepatitis C, *Exp. Opin. Investig. Drugs* 2003 12(8): 1269-1280; S.-L. Tan et al., Hepatitis C Therapeutics: Current Status and Emerging Strategies, *Nature Rev. Drug Discov.* 2002 1:867-881; R. De Francesco et al. Approaching a new era for hepatitis C virus therapy: inhibitors of the NS3-4A serine protease and the NS5B RNA-dependent RNA polymerase, *Antiviral Res.* 2003 58:1-16; Q. M. Wang et al. Hepatitis C virus encoded proteins: targets for antiviral therapy, *Drugs of the Future* 2000 25(9):933-8-944; J. A. Wu and Z. Hong, Targeting NS5B-Dependent RNA Polymerase for Anti-HCV Chemotherapy *Cur. Drug Targ.-Inf. Dis.* 2003 3:207-219. The reviews cite compounds presently in various stages of the development process. Combination therapy with two or three agents directed to the same or different targets has become standard therapy to avoid or slow the development of resistant strains of a virus and the compounds disclosed in the above reviews could be used in combination therapy with compounds of the present invention and these reviews are hereby incorporated by reference in their entirety.

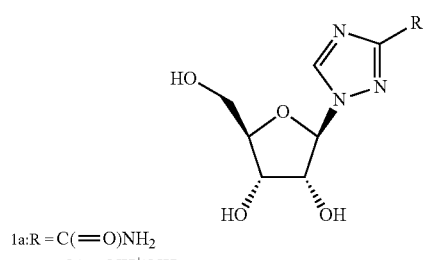

1a: R = C(=O)NH$_2$
1b: R = C(=NH$^+$)NH$_2$

Ribavirin (1a; 1-((2R,3R,4S,5R)-3,4-Dihydroxy-5-hydroxymethyl-tetrahydro-furan-2-yl)-1H-[1,2,4]triazole-3- carboxylic acid amide; VIRAZOLE®) is a synthetic, non-interferon-inducing, broad spectrum antiviral nucleoside analog. Ribavirin has in vitro activity against several DNA and RNA viruses including Flaviviridae (Gary L. Davis, *Gastroenterology* 2000 118:S104-S114). In monotherapy ribavirin reduces serum amino transferase levels to normal in 40% of patients, but it does not lower serum levels of HCV-RNA. Ribavirin also exhibits significant toxicity and is known to induce anemia. Ribavirin is an inhibitor of inosine monophosphate dehydrogenase. RiboviRin is not approved in monotherapy against HCV but the compound is approved in combination therapy with interferon α-2a and interferon α-2b. Viramidine 1b is a prodrug converted to 1a in hepatocytes.

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon β, type 2 includes interferon γ. Type 1 interferon is produced mainly by infected cells and protects neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (L.-B. Davis, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release,* 2001 72:217-224).

Interferon α-2a and interferon α-2b are currently approved as monotherapy for the treatment of HCV. ROFERON-A® (Roche) is the recombinant form of interferon α-2a. PEGASYS® (Roche) is the pegylated (i.e. polyethylene glycol modified) form of interferon α-2a. INTRON-A® (Schering Corporation) is the recombinant form of Interferon α-2b, and PEG-INTRON® (Schering Corporation) is the pegylated form of interferon α-2b.

Other forms of interferon α, as well as interferon β, γ, τ and ω are currently in clinical development for the treatment of HCV. For example, INFERGEN® (interferon alphacon-1) by InterMune, OMNIFERON® (natural interferon) by Viragen, ALBUFERON® by Human Genome Sciences, REBIF® (interferon β-1a) by Ares-Serono, Omega Interferon by Bio-Medicine, Oral Interferon Alpha by Amarillo Biosciences, and interferon γ, interferon τ, and interferon γ-1b by Inter-Mune are in development.

Combination therapy of HCV with ribavirin and interferon-α currently represent the optimal therapy. Combining ribavirin and PEG-IFN (infra) results in a sustained viral response in 54-56% of patients. The SVR approaches 80% for type 2 and 3 HCV. (Walker, supra) Unfortunately, the combination also produces side effects which pose clinical challenges. Depression, flu-like symptoms and skin reactions are associated with subcutaneous IFN-α and hemolytic anemia is associated with sustained treatment with ribavirin.

Other macromolecular compounds currently in preclinical or clinical development for treatment of hepatitis C virus infection include: Interleukin-10 by Schering-Plough, IP-SO1 by Interneuron, Merimebodib (VX-497) by Vertex, HEPTAZYME® by RPI, IDN-6556 by Idun Pharma., XTL-002 by XTL., HCV/MFS9 by Chiron, CIVACIR® (hepatitis C Immune Globulin) by NABI, ZADAXIN® (thymosin α-1) by SciClone, thymosin plus pegylated interferon by Sci-Clone, CEPLENE®; a therapeutic vaccine directed to E2 by Innogenetics, therapeutic vaccine by Intercell, therapeutic vaccine by Epimmune/Genencor, a therapeutic vaccine by Merix, a therapeutic vaccine, Chron-VacC, by Tripep.

Other macromolecular approaches include ribozymes targeted at HCV RNA. Ribozymes are short naturally occurring molecules with endonuclease activity that catalyze the sequence-specific cleavage of RNA. An alternate approach is the use of antisense oligonucleotides bind to RNA and stimulate RNaseH mediated cleavage.

A number of potential molecular targets for drug development as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell and be converted in vivo to its triphosphate form to compete as a substrate at the polymerase nucleotide binding site. This conversion to the triphosphate is commonly mediated by cellular kinases which impart additional structural limitations on any nucleoside. Nucleoside polymerases are also an essential component in normal cell division and to limit potential toxic side effects, nucleoside inhibitors should selectively inhibit viral polymerases without disrupting essential cellular growth and repair by inhibiting host polymerases. Thus the requirement for phosphorylation by endogenous kinases and selectivity with respect to endogenous polymerases imposes strict requirements on the structure of potential nucleoside therapeutics.

Nucleoside Prodrugs

While nucleosides often are potent anti-viral and chemotherapeutic agents, their practical utility is often limited by two factors. Firstly, poor pharmacokinetic properties frequently limit the absorption of the nucleoside from the gut and; secondly, suboptimal physical properties restrict formulation options which could be employed to enhance delivery of the active ingredient.

Albert introduced the term prodrug to describe a compound which lacks intrinsic biological activity but which is capable of metabolic transformation to the active drug substance (A. Albert, *Selective Toxicity*, Chapman and Hall, London, 1951). Produgs have been recently reviewed (P. Ettmayer et al., *J. Med Chem.* 2004 47(10):2393-2404; K. Beaumont et al., *Curr. Drug Metab.* 2003 4:461-485; H. Bundgaard, *Design of Prodrugs: Bioreversible derivatives for various functional groups and chemical entities in Design of Prodrugs*, H. Bundgaard (ed) Elsevier Science Publishers, Amersterdam 1985; G. M. Pauletti et al. *Adv. Drug Deliv. Rev.* 1997 27:235-256; R. J. Jones and N. Bischofberger, *Antiviral Res.* 1995 27; 1-15 and C. R. Wagner et al., *Med. Res. Rev.* 2000 20:417-45). While the metabolic transformation can catalyzed by specific enzymes, often hydrolases, the active compound can also be regenerated by non-specific chemical processes.

Pharmaceutically acceptable prodrugs refer to a compound that is metabolized, for example hydrolyzed or oxidized, in the host to form the compound of the present invention. The bioconversion should avoid formation fragments with toxicological liabilities. Typical examples of prodrugs include compounds that have biologically labile protecting groups linked to a functional moiety of the active compound. Alkylation, acylation or other lipophilic modification of the hydroxy group(s) on the sugar moiety have been utilized in the design of pronucleotides. These pronucleotides can be hydrolyzed or dealkylated in vivo to generate the active compound.

Factors limiting oral bioavailability frequently are absorption from the gastrointestinal tract and first-pass excretion by the gut wall and the liver. Optimization of transcellular absorption through the GI tract requires a $D_{(7.4)}$ greater than zero. Optimization of the distribution coefficient does not, however, insure success. The prodrug may have to avoid active efflux transporters in the enterocyte. Intracellular metabolism in the enterocyte can result in passive transport or active transport of the metabolite by efflux pumps back into the gut lumen. The prodrug must also resist undesired biotransformations in the blood before reaching the target cells or receptors.

High circulating levels of antiviral medications are frequently required to maintain sufficiently high blood levels of the API to minimize the risk of generating resistant populations. For example, recent trials have used doses of up to 1500 mg BID and QID of isobutyric acid (2R,3R,4R,5R)-5-(4-amino-2-oxo-2H-pyrimidin-1-yl)-4-fluoro-2-isobutyryloxymethyl-4-methyl-tetrahydro-furan-3-yl ester isobutyric acid (II: R7128). (S. Le Pogam et al., "No Evidence of R7128 Drug Resistance After Up To 4 Weeks Treatment of GT1,2 and 3 Hepatitis C Virus Infected Individuals", *44th Annual Meeting of the European Association for the Study of the Liver (EASL)*, Copenhagen, Denmark, Apr. 22-Apr. 26, 2009). This often results in high daily doses that require large pill or capsule size or more frequent administration of the dosage form. When high doses of an active pharmaceutical ingredient are required, the opportunity to add diluents or excipients to improve bioavailability is often limited. Thus the design of novel HCV polymerase inhibitors requires identifying compounds which are bioavailable, are converted to the corresponding triphosphate and are potent inhibitors of HCV polymerase.

The obligatory requirement for in vivo phosphorylation has recently led to interest in nucleoside monophosphate prodrugs containing a masked phosphate moiety which is susceptible to intracellular enzymatic activation leading to a nucleoside monophosphate. Since the rate limiting step in the formation of nucleoside triphosphates is the first step leading to a monophosphate, subsequent addition of the second and third phosphates form facilely from the monophosphate. (see, e.g., P. Perrone et al., *J. Med. Chem.*, 2007, 50(8):1840; S. J. Hecker and M. D. Erion, *J. Med Chem.* 2008 51(8):2328)

Chemical modification of an active compound to afford a potential prodrug produces an entirely new molecular entity which can exhibit undesirable physical, chemical and biological properties absent in the parent compound. Regulatory requirements for identification of metabolites may pose challenges if multiple pathways lead to a plurality of metabolites. Thus, the identification of prodrugs remains an uncertain and challenging exercise. Moreover, evaluating pharmacokinetic properties of potential prodrugs is a challenging and costly endeavor. Pharmacokinetic results from animal models may be difficult to extrapolate to humans.

The object of the present invention is to provide new compounds, methods and compositions for the treatment of a host infected with hepatitis C virus.

SUMMARY OF THE INVENTION

There is currently no preventive treatment or generally effective therapy for treating Hepatitis C virus (HCV) infections. Currently approved therapies, which exist only against HCV, have limited effectiveness and are associated with serious side effects. Design and development of new more effective therapies with less toxicity is, therefore, essential.

The present invention relates to compounds of formula I wherein:

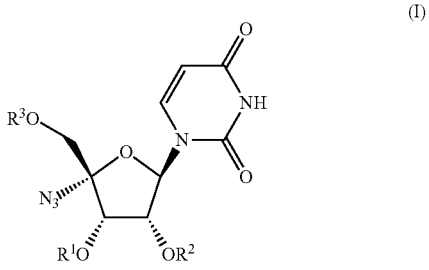

(I)

$R^1$ and $R^2$ are (i) independently in each occurrence selected from the group consisting of hydrogen, $C_{1-6}$ alkylcarbonyl, $C_{1-6}$ alkoxycarbonyl, and $C_{1-6}$ aminoalkylcarbonyl or (ii) taken together both $R^1$ and $R^2$ moieties together are C(=O).

$R^3$ is hydrogen, $C_{1-6}$ alkylcarbonyl, $C_{1-6}$ alkoxycarbonyl or $C_{1-6}$ aminoalkylcarbonyl.

a pharmaceutically acceptable salt thereof with the proviso that at least one of $R^1$, $R^2$ and $R^3$ are other than hydrogen.

The present invention also provides a method for treating a disease a Hepatitis C Virus (HCV) virus infection by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

Figure 1A:
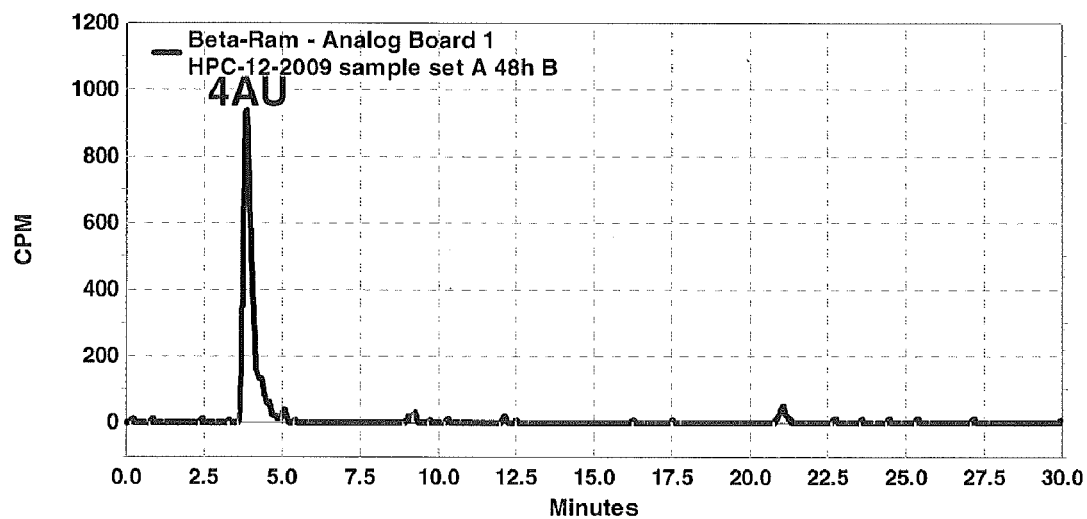
FIG. 1*a* depicts the phosphorylation profile of 4'-AU (4'-azido-uracil) in HCV replicon cells.
Figure 1B:
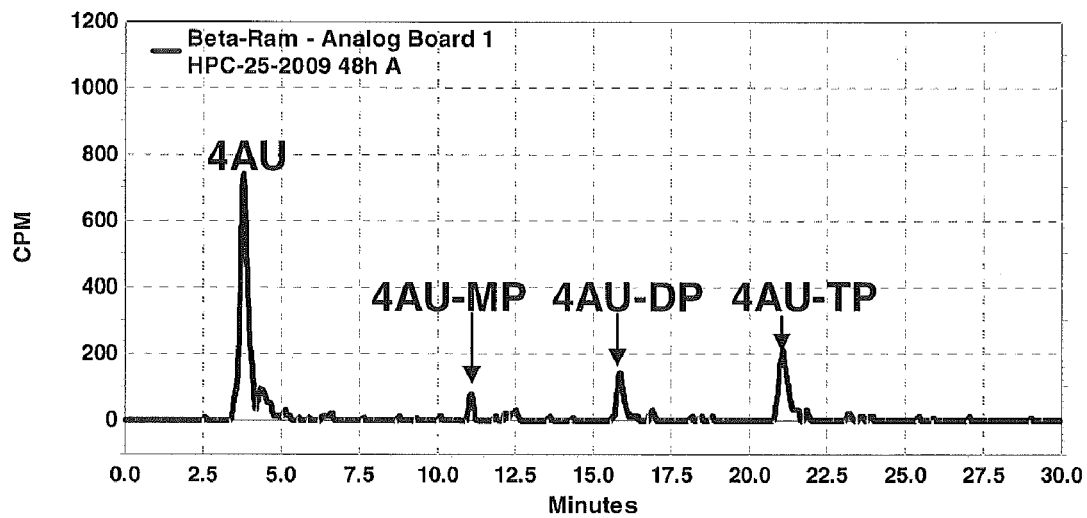
FIG. 1*b* depicts the phosphorylation profile of 4'-AU in human hepatocytes.

Triacyl derivatives of 4'-azido-cytidine (4'-AC) have been investigated as inhibitors of NS5B HCV polymerase. (K. Klumpp et al., *J. Bio. Chem.*, 2008 283(4):2167-2176) Unfortunately while 4'-AC is a potent inhibitor of viral replication, clinical studies terminated due to adverse side effects. The related pyrimidine nucleoside, 4'-azido-uridine (4'-AU), was inactive in the replicon assay which is widely used to evaluate potential polymerase inhibitors. (V. Lohmann et al., *J. Virol.* 2003 77:3007-3019, K. J. Blight et al., *Science* 2000 290 (5498):1870-1871). When the triphosphate was prepared chemically and evaluated in the HCV polymerase assay it inhibited the enzyme with a $K_i$ of 0.038±8 µM compared to a $K_i$ of 0.040±25 µM for 4'-azido-cytidine triphosphate. (D. Smith et al., *Bioorg. Med. Chem. Lett.* 2007 17:2570) The lack of activity in the replicon assay was attributed to failure of endogenous kinases to phosphorylate 4'-AU in vivo. This explanation was supported by the demonstration that while 4'-AC was phosphorylated in PBMC (peripheral blood mononuclear cells), 4'-AU was not (FIG. 1).

Figure 2A:
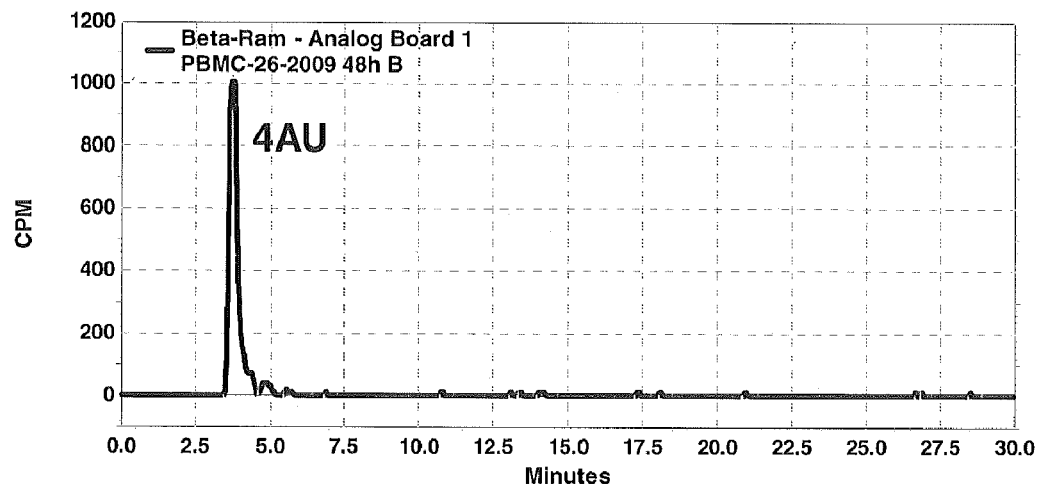
FIG. 2*a* depicts the phosphorylation profile of 4'-AU in PBMC.
Figure 2B:
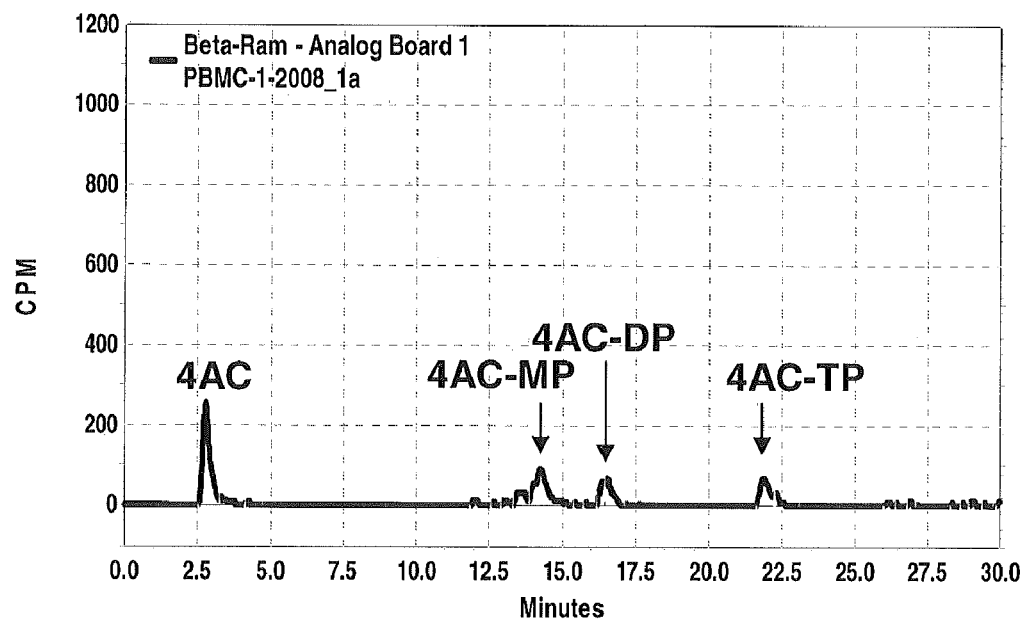
FIG. 2*b* and Fig. 2*c* depict the phosphorylation profile of 4'-azido-cytidine (4'-AC) in PBMC, after 1 h incubation and 120 h incubation, respectively.
Figure 2C:
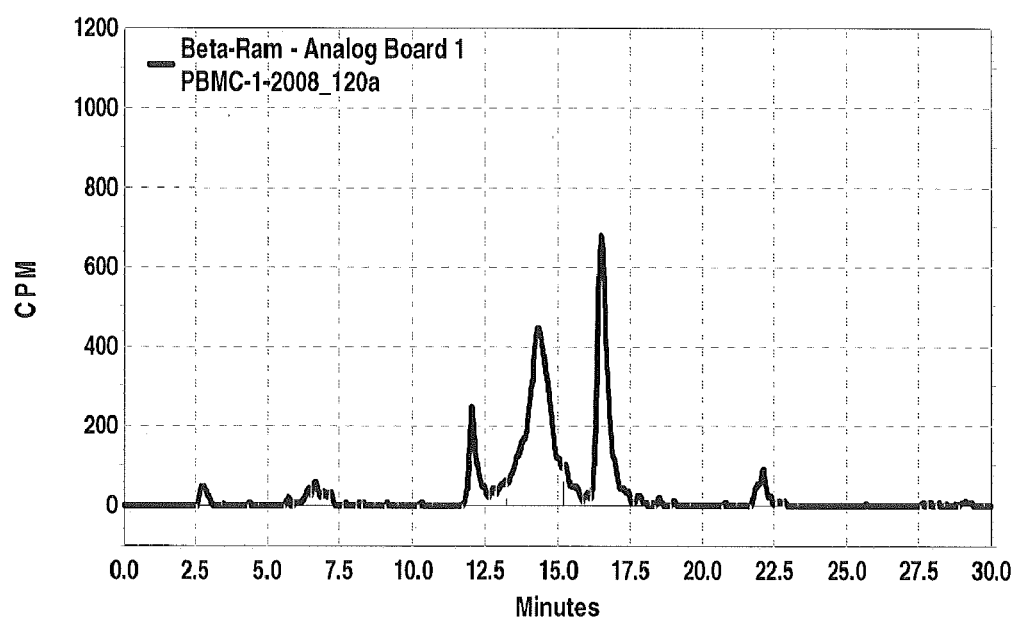

Now, surprisingly, it has been found that, in contrast to the lack of phosphorylation of 4'-AU in human hepatoma Huh7 cells used in the replicon assay, phosphorylation does occur efficiently in primary human hepatocytes. (FIG. 2) Since the cell specific phosphorylation takes place in the target tissue for HCV replication, there is the potential that 4'-AU will be selectively phosphorylated in the target tissue vis-à-vis other tissues thereby minimizing off target toxicity.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example: MeC(=O)OR$^4$ wherein

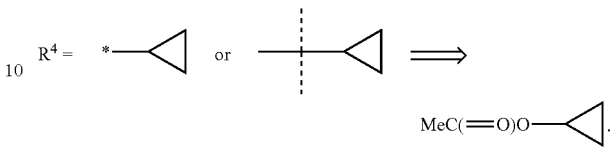

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇆ —C(—OH)=CH—), amide/imidic acid (—C(=O)—NH— ⇆ —C(—OH)=N—) and amidine (—C(=NR)—NH— ⇆ —C(—NHR)=N—) tautomers. The latter two are particularly common in heteroaryl and heterocyclic rings and the present invention encompasses all tautomeric forms of the compounds.

In one embodiment of the present invention there is provided a compound according to formula I wherein $R^1$, $R^2$ and $R^3$ are as described herein above.

In another embodiment of the present invention there is provided a compound according to formula I wherein $R^1$, $R^2$ and $R^3$ are $C_{1-6}$ alkylcarbonyl.

In another embodiment of the present invention there is provided a compound according to formula I wherein $R^1$ and $R^2$ are $C_{1-6}$ alkylcarbonyl and $R^1$ and $R^2$ is hydrogen.

In another embodiment of the present invention there is provided a compound according to formula I wherein $R^1$ and $R^2$ are hydrogen and $R^3$ $C_{1-6}$ alkylcarbonyl, or $C_{1-6}$ aminoalkylcarbonyl.

In another embodiment of the present invention there is provided a compound selected from compounds 14 to I-6 of TABLE I.

In another embodiment of the present invention there is provided a method of treating an HCV infection comprising administering to a patient in need thereof a therapeutically effective amount of a compound according to formula I wherein $R^1$, $R^2$ and $R^3$ are as defined hereinabove. In all other embodiments provided below, substituents which can be present in each embodiment and which are not explicitly defined retain the broadest definition provided in the Summary of the Invention.

In another embodiment of the present invention there is provided a method of treating an HCV infection comprising administering to a patient in need thereof a therapeutically effective amount of a compound according to formula I wherein $R^1$, $R^2$ and $R^3$ are $C_{1-6}$ alkylcarbonyl.

In another embodiment of the present invention there is provided a method of treating an HCV infection comprising administering to a patient in need thereof a therapeutically effective amount of a compound according to formula I wherein $R^1$ and $R^2$ are $C_{1-6}$ alkylcarbonyl and $R^3$ is hydrogen.

In another embodiment of the present invention there is provided a method of treating an HCV infection comprising administering to a patient in need thereof a therapeutically effective amount of a compound according to formula I wherein $R^1$ and $R^2$ are hydrogen and $R^3$ $C_{1-6}$ alkylcarbonyl, or $C_{1-6}$ aminoalkylcarbonyl.

In another embodiment of the present invention there is provided a method of treating an HCV infection comprising administering to a patient in need thereof a therapeutically effective amount of a compound according to formula I wherein $R^1$, $R^2$ and $R^3$ are as described herein above and co-administering at least one immune system modulator and/or at least one antiviral agent that inhibits replication of HCV.

In another embodiment of the present invention there is provided a method of treating an HCV infection comprising administering to a patient in need thereof a therapeutically effective amount of a compound according to formula I wherein $R^1$, $R^2$ and $R^3$ are as described herein above and co-administering at least one immune system modulator is selected from the group consisting of an interferon, interleukin, tumor necrosis factor and colony stimulating factor.

In another embodiment of the present invention there is provided a method of treating an HCV infection comprising administering to a patient in need thereof a therapeutically effective amount of a compound according to formula I wherein $R^1$, $R^2$ and $R^3$ are as described herein above and co-administering at least one immune system modulator wherein the immune system modulator is an interferon or chemically derivatized interferon.

In another embodiment of the present invention there is provided a method of treating an HCV infection comprising administering to a patient in need thereof a therapeutically effective amount of a compound according to formula I wherein $R^1$, $R^2$ and $R^3$ are as described herein above and co-administering at least one antiviral agent that inhibits replication of HCV.

In a fourteenth embodiment of the present invention there is provided a method of treating an HCV infection comprising administering to a patient in need thereof a therapeutically effective amount of a compound according to formula I wherein $R^1$, $R^2$ and $R^3$ are as described herein above and co-administering at least one antiviral agent selected from the group consisting of an HCV protease inhibitor, another nucleoside HCV polymerase inhibitor, a non-nucleoside HCV polymerase inhibitor, an HCV helicase inhibitor, an HCV primase inhibitor and an HCV fusion inhibitor.

In another embodiment of the present invention there is provided pharmaceutical composition comprising a therapeutically effective quantity of a compound according to formula I wherein $R^1$, $R^2$ and $R^3$ are as described herein above admixed with at least one pharmaceutically acceptable carriers, diluent or excipient.

The term or "alkylcarbonyl" as used herein denotes a group of formula C(=O)R wherein R is alkyl as defined herein. The term $C_{1-6}$ acyl [or "alkanoyl"] refers to a group —C(=O)R contain 1 to 6 carbon atoms. The $C_1$ acyl [or "alkanoyl"] group is the formyl group wherein R=H and a $C_6$ acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The terms "alkoxycarbonyl" and "aryloxycarbonyl" as used herein denotes a group of formula —C(=O)OR wherein R is alkyl or aryl respectively and alkyl and aryl are as defined herein.

The term "aminoalkylcarbonyl" as used herein refers to an alkylcarbonyl moiety as defined herein wherein one hydrogen is replaced by an amino group. The term $C_{1-6}$ aminoalkylcarbonyl specifies an $C_{1-6}$ alkylcarbonyl group. Examples of aminoalkylcarbonyl moieties include, but are not limited to, glycyl [COCH$_2$NH$_2$], alanyl [COCH(NH$_2$)Me], valinyl [COCH(NH$_2$)CHMe$_2$], leucinyl [COCH(NH$_2$)CH$_2$CHMe$_2$], isoleucinyl [COCH(NH$_2$)CHMeEt] and norleucinyl [COCH(NH$_2$)(CH$_2$)$_3$Me] and the like. This definition is not limited to naturally occurring amino acids.

Commonly used abbreviations include: acetyl (Ac), aqueous (aq.), 4AC (4-azidocytidine), 4AU (4-azidouridine), 4AU-MP (4-azidouridine monophosphate), 4AU-DP (4-azidouridine diphosphate), 4AU-TP (4-azidouridine triphosphate), atmospheres (Atm), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), ethyl (Et), ethanol (EtOH), 1-(3-dimethylaminopropyl)-3-ethylcarbodiimide hydrochloride (EDCI), ethyl acetate (EtOAc), 2-ethoxy-2H-quinoline-1-carboxylic acid ethyl ester (EEDQ), diethyl ether (Et$_2$O), acetic acid (HOAc), 1-N-hydroxybenzotriazole (HOBt), high pressure liquid chromatography (HPLC), iso-propanol (IPA), methanol (MeOH), melting point (mp), MeSO$_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tent-butyldimethylsilyl or t-BuMe$_2$Si (TBDMS), triethylamine (TEA or Et$_3$N), triflate or CF$_3$SO$_2$— (TI), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), p-toluenesulfonic acid monohydrate (TsOH or pTsOH), 4-Me-C$_6$H4SO$_2$— or tosyl (Ts), N-urethane-N-carboxyanhydride (UNCA). Conventional nomenclature including the prefixes normal (n-), iso (i-), secondary (sec-), tertiary (tent-) and neo- have their customary meaning when used with an alkyl moiety. (J. Rigaudy and D. P. Klesney, Nomenclature in Organic Chemistry, IUPAC 1979 Pergamon Press, Oxford).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

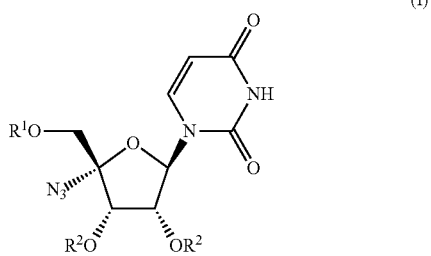

(I)

| Cpd No. | R$^1$ | R$^2$ | Method | MS (M + H)+ | MP |
|---|---|---|---|---|---|
| I-1 | H | EtC(=O) | C | 398 | 118-120 |
| I-2 | i-PrC(=O) | i-PrC(=O) | A | 496 | |
| I-3 | EtC(=O) | EtC(=O) | A | | 111-113 |
| I-4 | MeC(=O) | MeC(=O) | A | | 158 |
| I-5 | n-BuC(=O) | n-BuC(=O) | A | | 64 |
| I-6 | EtC(=O) | H | B | 340 [M − H] | 148-150 |
| I-7 | C$_7$H$_{15}$C(=O) | H | B | 412 | |

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, eg., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

Compounds of the present invention can be prepared by acylation of 4-azido-uracil (CASRN 139442-01-6) or a protected derivative thereof, e.g., the 2',3'-acetonide (CASRN 690271-27-3). Treating 4'AU with an activated carboxylic acid derivative such as an acid chloride or acid anhydride affords triacyl derivatives. Treating the corresponding acetonide affords the 5'-acyl derivative which is subsequently deprotected.

The term "protecting group" as used herein refers to a chemical group that (a) efficiently combines with a reactive group in a molecule; (b) prevents a reactive group from participating in an undesirable chemical reaction; and (c) can be easily removed after protection of the reactive group is no longer required. Protecting groups are used in synthesis to temporarily mask the characteristic chemistry of a functional group because it interferes with another reaction. Reagents and protocols for to introduce and remove protecting groups are well known and have been reviewed in numerous texts (e.g., T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 John Wiley and Sons, 1971-1996). One skilled in the chemical arts will appreciate that on occasion protocols must be optimized for a particular molecule and such optimization is well with the ability of one skilled in these arts.

2',3'-Diacyl-4'-AU derivatives were prepared by a enzymatic process. 5'-Acyl-4'-AU derivatives were prepared by acetylation of the 2',3'-acetonide of 4'-AU (example 3) or by a selective enzyme-catalyzed acylation of 4'-AU.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

Method A: Preparation of 2',3',5'-Triacyl Nucleoside Derivatives

Acetic acid, 3,4-diacetoxy-5-(4-amino-2-oxo-2H-pyrimidin-1-yl)-tetrahydro-furan-2-ylmethyl ester (22)

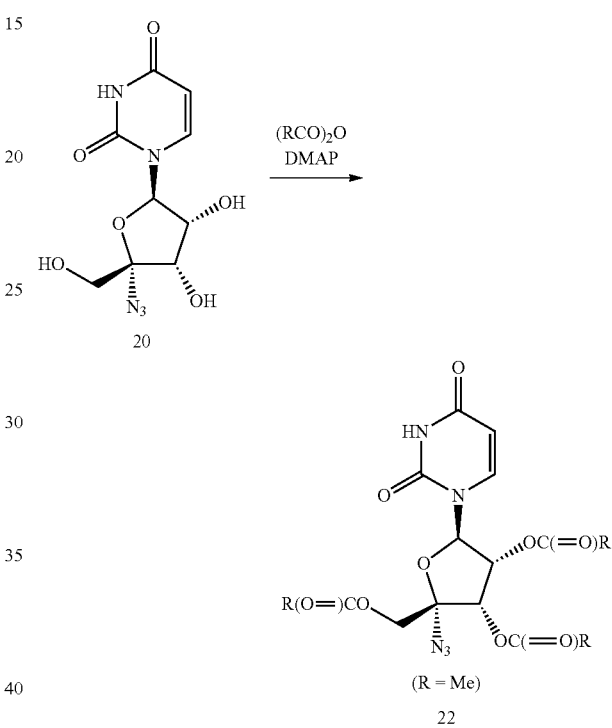

To a stirred solution containing 4'-azidouridine, (0.330 g, 1.15 mmol), pyridine (2 mL) and acetic anhydride (2 mL) was added DMAP (0.010 g, 0.08 mmol). After 12 h, the reaction mixture was evaporated to dryness under reduced pressure. The residue was dissolved in dichloromethane and washed with saturated aqueous sodium hydrogen carbonate solution, dried over magnesium sulfate and evaporated to dryness to give 0.42 g (88%) of 2',3',5'-tri-acetoxy-4'-azidouridine (22: R=CH$_3$, 1-4).

(2R,3S,4R,5R)-2-azido-5-(2,4-dioxo-3,4-dihydro-2H-pyrimidin-1-yl)-4-ethoxycarbonyloxy-2-ethoxycarbonyloxymethyl-tetrahydro-furan-3-yl-carbonic acid ester ethyl ester (22 R=OEt) can be prepared analogously except acetic anhydride is replaced by ethyl chloro-formate.

EXAMPLE 2

Method B: Preparation of 5'-Acyl Nucleoside Derivatives

Propionic acid (2R,3S,4R,5R)-2-azido-5-(2,4-dioxo-3,4-dihydro-2H-pyrimidin-1-yl)-3,4-dihydroxy-tetrahydro-furan-2-ylmethyl ester (I-6)

A 250 mL round bottom flask equipped with a magnetic stir bar was charged with 20 (5.94 g), vinyl propionate (15 mL) and THF (150 mL). Candida antarctica Lipase B (0.74 g, Sigma-Aldrich, recombinant from *Aspergillus oryzae*, 5865 U/g) immobilized on Immobead 150 was added and the reaction was heated to 60° C. under argon atmosphere. After 2 days, additional vinyl propionate (6 mL) and enzyme (1.11 g) was added, along with 10 g of 3 Å sieves. After an additional day, the reaction was filtered to remove the immobilized enzyme and concentrated in vacuo. The crude product was purified by $SiO_2$ chromatography eluting with an EtOAc/hexane gradient (50% to 100% EtOAc). A white foam (4 g) was obtained after solvent removal and drying under high vacuum. This material (3.25 g) was suspended in 3/1 hexanes/IPA and stirred 3 h at RT. The resultant crystalline material was collected by filtration and dried in a vacuum oven at 75° C. to afford 3.18 g of I-6: m.p. 148-150 C.

One skilled in the art will recognize that another general procedure to prepare 5'-acyl derivatives comprises acylation of 4'-C-azido-2',3'-O-(1-methylethylidene)-uridine (CASRN 690271-27-3) with acid chlorides and acid anhydrides and subsequently removing the isopropylidene protecting group under mild acidic conditions such as HCl in aqueous alcohols. (J. A. Martin et al., WO2004/046159 published Jun. 3, 2004 which is hereby incorporated by reference in its entirety).

EXAMPLE 3

Propionic acid (2R,3S,4R,5R)-2-azido-5-(2,4-dioxo-3,4-dihydro-2H-pyrimidin-1-yl)-3,4-dihydroxy-tetrahydro-furan-2-ylmethyl ester (I-6)—Alternative Procedure

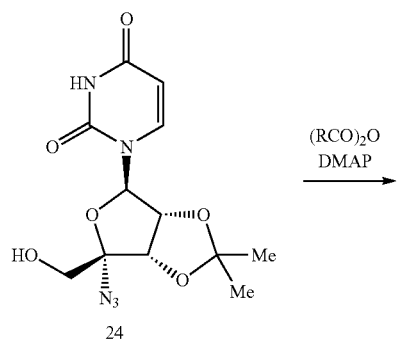

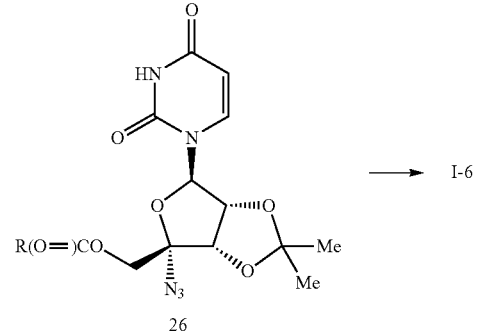

A 3-necked round-bottomed flask equipped with a bubbler, a stirrer, a thermometer and a ice cooling bath was charged with 24 (10 g, 30.7 mmol, Eq: 1.00, CASRN 139442-01-6), DMAP (376 mg, 3.07 mmol, Eq: 0.1), DIPEA (7.95 g, 10.7 mL, 61.5 mmol, Eq: 2.0), acetonitrile (47.2 g, 60.0 mL, Eq: -). The slurry was stirred 0.5 h. propionyl chloride (3.05 g, 2.86 mL, 32.3 mmol, Eq: 1.05) was added at 0-10° C. over 10 min. The reaction mixture became homogeneous and was warmed to RT. The reaction mixture was partitioned between $H_2O$ (30 mL) and EtOAc (50 mL) and the organic phase washed with 2N HCl (2×30 mL), sat'd. aq. $NaHCO_3$ (20 mL), brine (10 mL), dried, filtered and concentrated in vacuo to afford 15.2 g of an oil. 15.2 g. The product (5.37 g) thus obtained was dissolved in a solution of IPA (25 mL), 6N aq. HCl (12 mL) and hydroxylamine hydrochloride (0.8 g). The reaction mixture was stirred at RT. The reaction was stirred for 5 h, partitioned between $H_2O$ (30 mL), DCM (50 mL) The organic layer was washed sequentially with sat'd. aq. $NaHCO_3$ (30 mL), water (10 mL), dried filtered and concentrated in vacuo. The residue was triturated with heptane (30 mL) to afford 1.27 g of I-6 as a foam.

EXAMPLE 4

Method C: Preparation of 2',3'-Diacyl Nucleoside Derivatives

Propionic acid (2R,3R,4S,5R)-5-azido-2-(2,4-dioxo-3,4-dihydro-2H-pyrimidin-1-yl)-5-hydroxymethyl-4-propionyloxy-tetrahydro-furan-3-yl ester (I-1)

(2R,3S,4R,5R)-2-azido-5-(2,4-dioxo-3,4-dihydro-2H-pyrimidin-1-yl)-3,4-bis-propionyloxy-tetrahydro-furan-2-yl methyl propionate (28) is prepared as described in example 1 except acetic anhydride is replaced with propionyl chloride or propionic anhydride To a solution of 28 (4.42 g) dissolved in hot (ca. 40° C.) MTBE (20 mL) was added phosphate buffer (27 mL, pH=6.5) and brine (0.5 mL). Lipolase enzyme solution (5 ml) was added and the reaction mixture was stirred at 30-35° C. for ca. 3 h. The rate of hydrolysis was found to be quite slow. Additional enzyme solution (6 ml) was added, and the reaction mixture was stirred at 30-35° C. for 3 days to achieve about 95% conversion. The reaction mixture was extracted with EtOAc (30 mL). An emulsion formed during extraction that was resolved by addition of methanol (ca. 10 mL) The organic extract was washed with brine and water and then evaporated to dryness to 5.7 g oil (89% crude yield, ca. 94% dipropionate by area normalized HPLC). The viscous oil was further dried in a vacuum oven at about 50° C. to obtain a foam. The crude product was further purified by $SiO_2$ chromatography eluting with a MeOH/DCM gradient to afford I-1 as a waxy solid that crystallized upon standing.

EXAMPLE 5

(R)-2-Amino-3-methyl-butyric acid (2R,3S,4R,5R)-2-azido-5-(2,4-dioxo-3,4-dihydro-2H-pyrimidin-1-yl)-3,4-dihydroxy-tetrahydro-furan-2-ylmethyl ester step 1—To a stirred solution containing 24 (1.00 g, 3.07 mmol), Boc-(L)-valine (6.14 mmol) and EDCI (6.14 mmol) in DMF (20 mL) is added DMAP (3.07 mmol) of DMAP. The resulting solution is stirred under an atmosphere of nitrogen and at RT. After 12 h, the reaction mixture is evaporated to dryness under reduced pressure. The crude product is purified by $SiO_2$ chromatography eluting with an EtOAc/hexane gradient to afford 24 (R=CH(NHBoc)CHMe$_2$).

step 2—The Boc and acetonide protecting groups can be removed in a solution of TFA and DCM or HCl and dioxane or methanol.

EXAMPLE 6

Plasma Pharmacokinectics

Pharmacokinetic procedures were used to determine plasma levels of 4-amino-1-((2R,3R,4S,5R)-5-azido-3,4-dihydroxy-5-hydroxymethyl-tetrahydro-furan-2-yl)-1H-pyrimidin-2-one (II) after administration of a single oral 5 mg/kg dose of a prodrug of II. The formulation is a solution/suspension containing 0.0176 mmol of prodrug in 5 mL of an appropriate vehicle.

Three unfasted male Cynomolgus monkeys (6-9 kg) were fitted with a saphenous or brachial catheter to facilitate blood draw. Free access to food and water will be allowed at all times during the study. On the day of the study a predose blood sample (2-3 mL) was taken from each monkey. The monkeys were dosed with 1 mL/kg of the dose solution by oral gavage. At each of the following time points (0.25, 0.5, 1, 3, 5, 7, 10, 24, 32, and 48 hour) after dosing, approximately 0.5 mL of blood will be collected into lithium heparin-coated tubes. Blood was centrifuged to obtain plasma which was frozen until analysis.

The concentration of Ia ($R^1$-$R^4$=H) in each plasma sample was determined by an LC-MS assay. Standard curves were prepared in blank monkey plasma. The AUC represents the area under a plot of concentration vs time total which describes the concentration of the drug in systemic circulation as a function of time (L. Z. Benet, D. L. Kroetz and L. B. Sheiner Pharmacokinetics in Goodman & Gilman's The Pharmacological Basis of Therapeutics, J. G. Hardman & L. E. Limbird Eds., 9$^{th}$ Edition, McGraw Hill, N.Y., p 17-23). Cmax is the peak concentration which is found.

|  |  | 4'-AU | |
|---|---|---|---|
| Cpd. No. | Dose [2] mg/kg | $C_{max}$ (µg/mL) | AUC (h*µg/mL) |
| 4'-AU [1] | 10 | 3.1 | 43 |
| I-1 | * | 9.2 | 101 |
| I-3 | * | 5.0 | 75 |
| 4'-AU | 300 | 22.0 | 328 |
| I-1 | * | 85.7 | 1420 |
| I-3 | * | 55.5 | 1020 |

[1] 4-azidouridine
* Dose of I-1 and I-3 is a molar equivalent to the dose of 4'AU

EXAMPLE 7

HCV NS5B RNA Polymerase Activity

Nucleoside monophosphates can be prepared according to the general procedure described by M. Yoshikawa et al., Tetrahedron Lett. 1967 50:5065-5068. methods for the preparation of nucleoside triphosphates also have been reviewed. (K. Burgess and Dan Cook, Chem. Rev. 2000 100:2047)

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570n-Con1 at the end of the reaction was directly proportional to the amount of light emitted by the scintillant.

The HCV polymerase used in the enzymatic activity assay is a 21 amino acid C-terminal deletion of full-length HCV polymerase derived from HCV Con1 strain, genotype 1b (GenBank accession number AJ242654) (NS5B570n-Con1). The NS5B570n-Cont was sub-cloned downstream to the T7 promoter of the plasmid expression construct pET17b and transformed into E. coli strain BL21(DE3) pLysS for protein expression. A single colony was used to start an innoculum for a 10 L culture in LB media supplemented with 100 µg/mL ampicillin at 37° C. Protein expression was induced by the addition of 0.25 mM isopropyl-β-D-thiogalactopyranoside (IPTG) when the optical density of the culture at 600 nM was 0.8. Induction of protein expression was carried out at 30° C. for 16 h after which the cells were harvested by centrifugation. NS5B570n-Con1 was purified to homogeneity using a three-column purification protocol including subsequent column chromatography on Ni—NTA, SP-Sepharose HP and Superdex 75 resins.

Enzymatic reactions in the presence of cIRES RNA template (see section 0004) contained 20 nM cIRES RNA, 20 nM NS5B570n-Con1 enzyme, 0.5 µCi of tritiated UTP (Perkin Elmer catalog no. TRK-412; specific activity: 30 to 60 Ci/mmol;), 1 µM each ATP, CTP, and GTP, 40 mM Tris-HCl pH 8.0, 40 mM NaCl, 4 mM DTT (dithiothreitol), 4 mM MgCl2, 5 µl of compound serial diluted in DMSO, and nuclease-free water to a final reaction volume of 50 µl. Enzymatic reactions in the presence of poly A RNA template (see section 0004) contained 20 nM Poly A:oligo(rU)16 premixed (see section 0004), 20 nM NS5B570n-Con1 enzyme, 1 µCi of tritiated UTP (Perkin Elmer catalog no. TRK-412; specific activity: 30 to 60 Ci/mmol), 40 mM Tris-HCl pH 8.0, 40 mM NaCl, 4 mM DTT (dithiothreitol), 4 mM MgCl2, 5 µl of compound serial diluted in DMSO, and nuclease-free water to a final reaction volume of 50 µl. Reaction mixtures were assembled in 96-well filter plates (cat # MADVNOB, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) was added to each reaction well.

Two RNA templates were used to assay compounds described herein. The cIRES RNA template was 377nucleotide long and consisted of a partial complementary sequence (36 nucleotides) of the core protein, followed by 341 nucleotide of the complementary sequence of the internal ribosome entry site. The poly A RNA template (GE Amersham catalog number 27-4110) was a homopolymeric RNA pre-annealed to a oligo(rU)16 primer at a molar ratio of 3-to-1 (primer-template).

The amount of light emitted from the scintillant was converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data was analyzed in Excel® (Microsoft®) and Activity-Base® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% ($IC_{50}$) was calculated by fitting $$Y = \% \text{ Min} + \frac{(\% \text{ Max} - \% \text{ Min})}{\left[1 + \frac{X}{(IC_{50})^S}\right]} \quad \text{(i)}$$

equation (i) to the data where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

The experimental value for the $IC_{50}$ of 4'-AU triphosphate is 0.46±0.088 μM which is similar to 4'-AC-triphosphate which is 29±0.13 μM.

EXAMPLE 8

Formation of 4AU-triphosphate in human hepatocytes, peripheral blood mononuclear cells (PBMCs), and bone marrow cells (BMCs)

The analysis of uptake and phosphorylation of the nucleoside analog 4AU in primary human hepatocytes was performed as previously published (Ma, H. et al. J. Biol. Chem. 2007, 282:29812-29820). Fresh human hepatocytes were plated and incubated with $^3$H-labeled 4AU for different time spans. At the time of cell harvest the cell culture medium was aspirated, and the cells were washed once with cold phosphate-buffered saline. The cells were scraped into 1 mL of pre-chilled 60% (v/v) methanol containing 10 mM EDTA and extracted in methanol for 24 h at −20° C. The extracted samples were then centrifuged at 10,000×g for 15 min to remove cell debris. The supernatant was transferred to new tubes and evaporated in a speed vacuum at room temperature. The dried pellets of cell extracts were dissolved in $H_2O$. Before HPLC analysis, cell extract samples were spiked with unlabeled reference standards 4AU and 4AU-mono-, di- and triphosphate derivatives.

The uptake and phosphorylation of 4AU in human peripheral blood mononuclear cells (PBMCs) and bone marrow cells (BMCs) were carried out by incubation of PBMC or BMC cell suspensions at 2-4×10$^5$ cells/ml or 5-6×10$^5$ cells/ml respectively with $^3$H-RO1080713 for different length of time. Cell culture media containing $^3$H-RO1080713 were replenished every 24 h. Duplicate samples equivalent to 2×10$^6$ viable cells per time point were harvested at the end of the experiments, pelleted by centrifugation for 5 min, and washed once with cold PBS. The final cell pellets were snap frozen on dry ice and stored at −80° C. until extraction. The extraction of the cell pellets was carried out as that for the primary hepatocytes.

The phosphorylation derivatives of 4AU were separated by ion exchange HPLC with a Whatman Partisil 10 SAX (4.6× 250 mm) column coupled to a radiometric detector (β-RAM, IN/US Systems, Inc.). The mobile phase gradient changed linearly from 99% buffer A ($H_2O$) and 1% buffer B (0.5 M $KH_2PO_4$+0.8 M KCl) to 100% buffer B between 4 and 16 minutes. 100% buffer B ran from 16 minutes to 26 minutes and changed back to 100% A in 1 minute. Buffer A ran until 32 minutes. The flow rate throughout the 32 minutes run was constant at 1 ml/min. A ratio of 5:1 Ultima-Flo™ AP (PerkinElmer) to column eluent was used.

The RO1080713 derivatives in the samples were identified by comparison of the retention times of the radioactive metabolites in the radiochromatogram with the retention times of the non-radioactive reference standards spiked in samples.

Figure 3A:
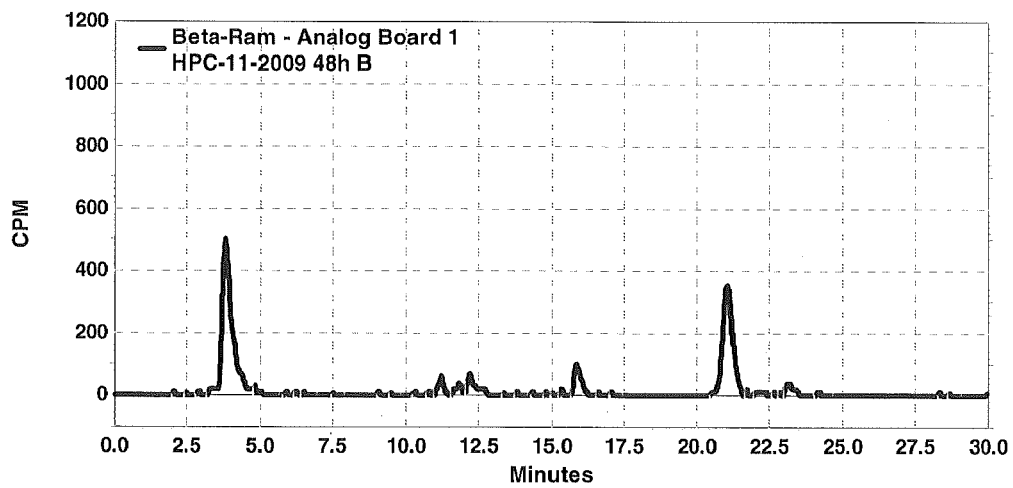
FIGS. 3*a*, 3*b* and 3*c* afford a comparison of the phosphorylation profile in primary human hepatocytes, bone marrow cells and PBMC, respectively after incubation of 2 a μM solution for 48 h. Similar profiles were obtained in 3 donors.
Figure 3B:
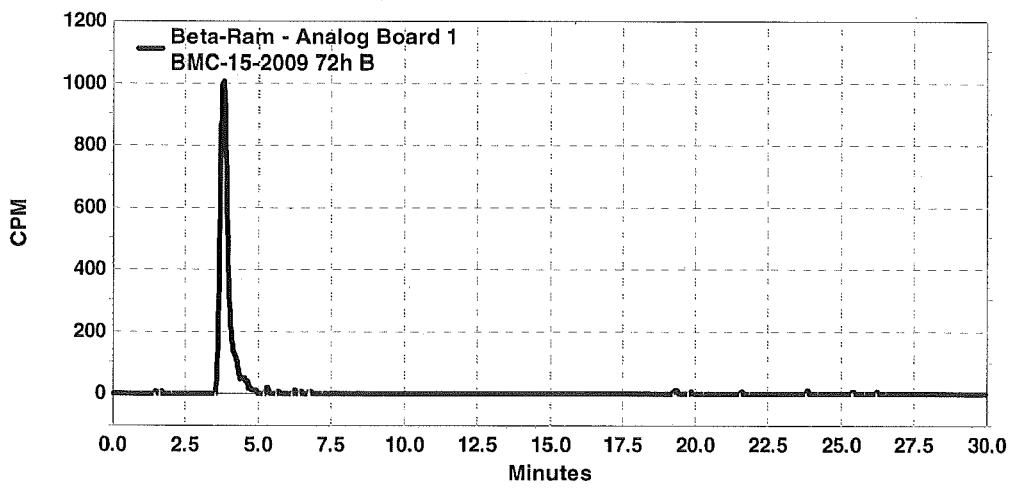
Figure 3C:
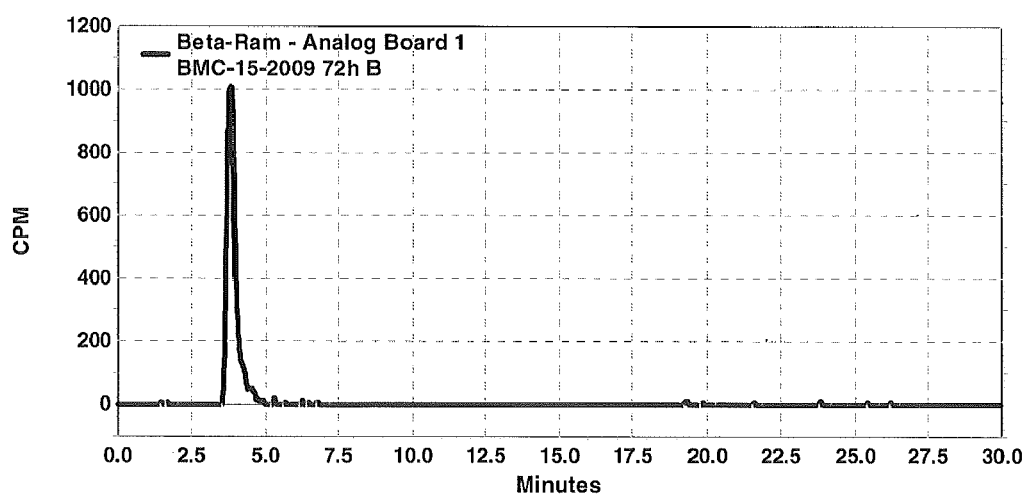
Figure 4:
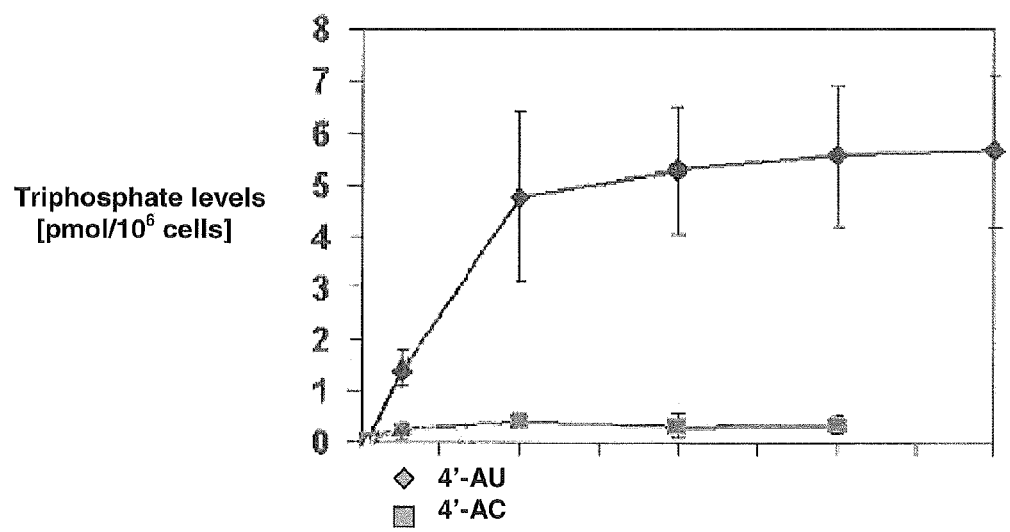
FIG. 4 depicts the efficiency of 4'AU vs. 4'AC in human hepatocytes.

FIG. 3 graphically illustrates the efficient phosphorylation of 4'-AU which is approximately 10-fold higher than 4'-AC.

EXAMPLE 9

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I

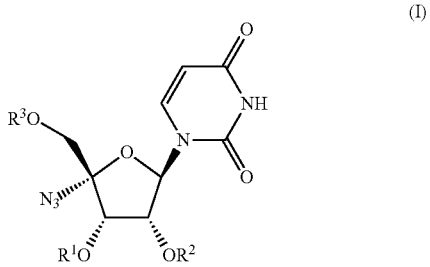

wherein:
R$^1$ and R$^2$ are (i) independently in each occurrence selected from the group consisting of hydrogen, C$_{2-6}$ alkylcarbonyl, C$_{1-6}$ alkoxycarbonyl, and C$_{1-6}$ aminoalkylcarbonyl or (ii) taken together both R$^1$ and R$^2$ moieties together are C(=O);
R$^3$ is hydrogen, C$_{2-6}$ alkylcarbonyl, C$_{1-6}$ alkoxycarbonyl or C$_{1-6}$ aminoalkylcarbonyl or, a pharmaceutically acceptable salt thereof with the proviso that at least one of R$^1$, R$^2$ and R$^3$ are other than hydrogen.

2. A compound according to claim 1 wherein R$^1$, R$^2$ and R$^3$ are C$_{2-6}$ alkylcarbonyl.

3. A compound according to claim 1 wherein R$^1$ and R$^2$ are C$_{2-6}$ alkylcarbonyl and R$^3$ is hydrogen.

4. A compound according to claim 1 wherein R$^1$ and R$^2$ are hydrogen and R$^3$ C$_{1-6}$ alkylcarbonyl, or C$_{1-6}$ aminoalkylcarbonyl.

5. A compound according to claim 1 wherein the compound is selected from the group consisting of:
propionic acid (2R,3R,4S,5R)-5-azido-2-(2,4-dioxo-3,4-dihydro-2H-pyrimidin-1-yl)-5-hydroxymethyl-4-propionyloxy-tetrahydro-furan-3-yl ester;
isobutyric acid (2R,3R,4S,5R)-5-azido-2-(2,4-dioxo-3,4-dihydro-2H-pyrimidin-1-yl)-4-isobutyryloxy-5-isobutyryloxymethyl-tetrahydro-furan-3-yl ester;
propionic acid (2R,3S,4R,5R)-2-azido-5-(2,4-dioxo-3,4-dihydro-2H-pyrimidin-1-yl)-3,4-bis-propionyloxy-tetrahydro-furan-2-ylmethyl ester;
pentanoic acid (2R,3S,4R,5R)-2-azido-5-(2,4-dioxo-3,4-dihydro-2H-pyrimidin-1-yl)-3,4-bis-pentanoyloxy-tetrahydro-furan-2-ylmethyl ester; and,
propionic acid (2R,3S,4R,5R)-2-azido-5-(2,4-dioxo-3,4-dihydro-2H-pyrimidin-1-yl)-3,4-dihydroxy-tetrahydro-furan-2-ylmethyl ester.

6. A method for treating Hepatitis C Virus (HCV) infection comprising treating a patient infected with HCV with a therapeutically effective quantity of a compound according to claim 1.

7. A method according to claim 6 wherein R$^1$, R$^2$ and R$^3$ are C$_{2-6}$ alkylcarbonyl.

8. A method according to claim 6 wherein R$^1$ and R$^2$ are C$_{2-6}$ alkylcarbonyl and R$^3$ is hydrogen.

9. A method according to claim 6 wherein R$^1$ and R$^2$ are hydrogen and R$^3$ is C$_{2-6}$ alkylcarbonyl or C$_{1-6}$ aminoalkylcarbonyl.

10. The method according to claim 6 further comprising administering at least one immune system modulator and/or at least one antiviral agent that inhibits replication of HCV.

11. The method according to claim 10 wherein the immune system modulator is selected from the group consisting of an interferon, interleukin, tumor necrosis factor and colony stimulating factor.

12. The method according to claim 11 wherein the immune system modulator is an interferon or chemically derivatized interferon.

13. The method according to claim 10 further comprising administering at least one other antiviral agent.

14. The method according to claim 13 wherein the antiviral compound is selected from the group consisting of an HCV protease inhibitor, another nucleoside HCV polymerase inhibitor, a non-nucleoside HCV polymerase inhibitor, an HCV helicase inhibitor, an HCV primase inhibitor and an HCV fusion inhibitor.

15. A pharmaceutical composition comprising a therapeutically effective quantity of a compound according to claim 1 admixed with at least one pharmaceutically acceptable carriers, diluent or excipient.

* * * * *